US007749735B2

(12) United States Patent
Schreiber

(10) Patent No.: US 7,749,735 B2
(45) Date of Patent: Jul. 6, 2010

(54) IFNAR2 MUTANTS, THEIR PRODUCTION AND USE

(75) Inventor: Gideon Schreiber, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 10/500,521

(22) PCT Filed: Dec. 31, 2002

(86) PCT No.: PCT/IL02/01059

§ 371 (c)(1),
(2), (4) Date: Feb. 18, 2005

(87) PCT Pub. No.: WO03/059950

PCT Pub. Date: Jul. 24, 2003

(65) Prior Publication Data

US 2005/0164185 A1    Jul. 28, 2005

(30) Foreign Application Priority Data

Dec. 31, 2001 (IL) ..................................... 147414

(51) Int. Cl.
  *C12P 19/00* (2006.01)
  *C12N 5/07* (2010.01)
  *C07K 14/00* (2006.01)
(52) U.S. Cl. ..................... 435/69.51; 435/326; 530/351
(58) Field of Classification Search .............. 435/69.51, 435/326; 530/351
  See application file for complete search history.

(56) References Cited

U.S. PATENT DOCUMENTS

| 4,588,585 | A | 5/1986 | Mark et al. |
| 4,737,462 | A | 4/1988 | Mark et al. |
| 4,904,584 | A | 2/1990 | Shaw |
| 4,959,314 | A | 9/1990 | Mark et al. |
| 4,965,195 | A | 10/1990 | Namen et al. |
| 5,017,691 | A | 5/1991 | Lee et al. |
| RE33,653 | E | 7/1991 | Mark et al. |
| 5,116,943 | A | 5/1992 | Koths et al. |
| 2001/0014333 | A1* | 8/2001 | Campbell et al. ......... 424/192.1 |

FOREIGN PATENT DOCUMENTS

| EP | 0220 574 | | 5/1987 |
| EP | 0679717 | B1 | 8/1999 |
| EP | 1037658 | B1 | 6/2002 |
| WO | WO 99/32141 | A1 | 7/1999 |
| WO | WO 00/22146 | | 4/2000 |
| WO | WO 00/24417 | * | 5/2000 |

OTHER PUBLICATIONS

Piehler, J. et al. J.Mol. Biol. 294:223-237, 1999.*
Pfeffer et al. Conference on Interferon Therapy of Multiple Sclerosis pp. 1-39, 1997—Abstract.*
Bowie, et al. Science, 247: 1306-10, 1990.*
Skolnick et al. TIBTECH 18:34-39, 2000.*
Hosaka et al. J. Biochem. 140:777-783; 2006.*
Alam, J., et al., "Comparative Pharmacokinetics and Pharmacodynamics of Two Recombinant Human Interferon Beta-1a (IFNβ-1a) Products Administered Intramuscularly in Healthy Male and Female Volunteers", Pharmaceutical Research, vol. 14, No. 4 (1997).
Anfinsen, C., "Principles that Govern the Folding of Protein Chains," Science, vol. 181, No. 4096, Jul. 20, 1973.
Baron, S., et al., "The Interferons: Mechanisms of Action and Clinical Applications," JAMA, vol. 266, No. 10, pp. 1375-1383, Sep. 11, 1991.
Baron, S., et al., "The Interferons: a Biological System with Therapeutic Potential in Viral Infections," Antiviral Research, vol. 24, pp. 97-110 (1994).
Chill, J., et al., "The Human Interferon Receptor: NMR-Based Modeling, Mapping of the IFN-α2 Binding Site, and Observed Ligand-Induced Tightening," Biochemistry, vol. 41, pp. 3575-3585 (2002).
Christofinis, G., et al., "Interferon Production by Human Lymphoblastoid Cell Lines of Different Origins," J. Gen. Virol., vol. 52, pp. 169-171 (1981).
Colamonici, O., et al., "Identification of a Novel Subunit of the Type I Interferon Receptor Localized to Human Chromosome 21," The Journal of Biological Chemistry, vol. 268, No. 15, pp. 10895-10899, May 25, 1993.
Colamonici, O., et al., "Multichain Structure of the IFN-α Receptor on Hematopoietic Cells," The Journal of Immunology, vol. 148, No. 7, pp. 2126-2132, Apr. 1, 1992.
Curtis, B., et al., "Enhanced Hematopoietic Activity of a Human Granulocyte/Macrophage Colony-Stimulating Factor-Interleukin 3 Fusion Protein," Proc. Natl. Acad. Sci. USA, vol. 88, pp. 5809-5813 (Jul. 1991).
Cusi, M., et al., "Harlequin Granulocyte-Colony Stimulating Factor Interleukin 6 Molecules with Bifunctional and Antagonistic Activities," Immunotechnology, vol. 3, pp. 61-69 (1997).
Domanski, P., et a., "Cloning and Expression of a Long Form of the β Subunit of the interferon αβ Receptor That is Required for Signaling," The Journal of Biological Chemistry, vol. 270, No. 37, pp. 21606-21611, Sep. 15, 1995.
Dron et al., "Interferon αβ Gene Structure and Regulation in Interferon: Principals and Medical Applications," Baron et al., Editors, University of Texas Medical Branch: Galveston, TX, pp. 33-45 (1992).
Duncan, G., et al., "The Transcription Factor Interferon Regulatory Factor-1 Is Essential for Natural Killer Cell Function in Vivo," J. Exp. Med., vol. 184, pp. 2043-2048 (Nov. 1996).
Edgington, S., "Biotech Products as Drug Leads", *Biotechnology*, vol. 13, p. 649 (Jul. 1995).

(Continued)

Primary Examiner—Fereydoun G Sajjadi
(74) Attorney, Agent, or Firm—Howrey LLP

(57) ABSTRACT

The present invention relates to mutant polypeptides of the beta chain of the type I IFN receptor (IFNAR2 mutant) with enhanced affinity for IFNβ as compared to the wild type protein for prolonging the effect of IFNβ in vivo.

18 Claims, 4 Drawing Sheets

OTHER PUBLICATIONS

Ezekowitz, R., et al., "Interferon α/β Selectively Antagonises Down-Regulation of Mannosyl-Fucosyl Receptors on Activated Macrophages by Interferon," Biochemical and Biophysical Research Communications, vol. 136, No. 2, pp. 737-744, Apr. 29, 1986.
Fierlbeck, G., et al., "Pharmacodynamics of Recombinant IFN-β During Long-Term Treatment of Malignant Melanoma," Journal of Interferon and Cytokine Research, vol. 16, pp. 777-781 (1996).
Grantham R., Amino Acid Difference Formula to Help Explain Protein Evolution, Science, vol. 185, pp. 862-864, Sep. 6, 1974.
Ibanez, C., et al., "Chimeric Molecules With Multiple Neurotrophic Activities Reveal Structural Elements Determining the Specificities of NGF and BDNF", The EMBO Journal., vol. 10, No. 8, pp. 2105-2110 (1991).
Jacobs, L., et al., "Intrathecally Administered Natural Human Fibroblast Interferon Reduces Exacerbations of Multiple Sclerosis," Arch Neurol., vol. 44, pp. 589-595 (Jun. 1987).
Keown, W., et al., "Methods for Introducing DNA into Mammalian Cells," Methods in Enzmology, vol. 185, pp. 527-537 (1990).
Lengyel, P., "Biochemistery of Interferons and Their Actions," Ann. Rev. Biochem., vol. 51, pp. 251-282, (1982).
Lewerenz, M., et al., "Shared Receptor Components but Distinct Complexes for α and β Interferons," J. Mol. Biol., vol. 282, pp. 585-599 (1998).
Lutfalla, G., "Mutant U5A Cells Are Complemented by an Interferon-αβ Receptor Subunit Generated by Alternative Processing of a New Member of a Cytokine Receptor Gene Cluster", The EMBO Journal, vol. 14, No. 20, pp. 5100-5108 (1995).
Novick, D., et al., "Soluble Interferon-α Receptor Molecules are Present in Body Fluids," FEBS, vol. 314, No. 3, pp. 445-448 (Dec. 1992).
Novick, D., et al., "Soluble and Membrane-Anchored Forms of the Human IFN-α/β Receptor," Journal of Leukocyte Biology, vol. 57, pp. 712-718 (May 1995).
Novick, D., et al., "The Human Interferon α/β Receptor: Characterization and Molecular Cloning," Cell, vol. 77, pp. 391-400, May 6, 1994.
Olins, P., et al., "Recent Advances in Heterologous Gene Expression in *Escherichia Coli*", Current Opinion in Biotechnology, vol. 4 (5), pp. 520-525 (1993).
Pestka, S., et al., "Interferons and Their Actions," Ann. Rev. Biochem., vol. 56, pp. 727-777 (1987).
Piehler, J., et al., "Mutational and Structural Analysis of the Binding Interface between Type I Interferons and their Receptor Ifnar2," J. Mol. Biol., vol. 294, No. 1, pp. 223-237 (1999).
Piehler, J., "Fast Transient Cytokine-Receptor Interactions Monitored in Real Time by Reflectometric Interference Spectroscopy," Analytical Biochemistry, vol. 289, pp. 173-186 (2001).
Piehler, J., et al., "Biophysical Analysis of the Interaction of Human Ifnar2 Expressed in *E. coli* with IFNα2," J. Mol. Biology, vol. 289, pp. 57-67 (1999).
Platanias L., et al., "Differences in Interferon α and β Signaling," The Journal of Biological Chemistry, vol. 271, No. 39, pp. 23630-23633, Sep. 27, 1996.
Platanias, L., et al., "Characterization of the α Subunit of the IFN-α Receptor," The Journal of Immunology, vol. 150, No. 8, pp. 3382-3388, Apr. 15, 1993.
Platanias, L., et al., "Tyrosine Phosphorylation of the α and β Subunits of the Type 1 Interferon Receptor," J. Biol. Chem. 269 (27): pp. 17761-17764 (Jul. 1994).
Qureshi, S., et al., "Function of Stat2 Protein in Transcriptional Activation by Alpha Interferon," Molecular and Cellular Biology, vol. 16, No. 1, pp. 288-293 (Jan. 1996).
Reff, Mitchell, "High-Level Production of Recombinant Immunoglobulins in Mammalian Cells," Current Opinion in Biotechnology, vol. 4, pp. 573-576 (1993).
Reuveny S., et al., "Effect of Temperature and Oxygen on Cell Growth and Recombinant Protein Production in Insect Cell Cultures," Appl. Microbiol. Biotechnol., vol. 38, pp. 619-623 (1993).
Roisman, L., et al., "Structure of the Interferon-Receptor Complex Determined by Distance Constraints from Double-Mutant Cycles and Flexible Docking," PNAS, vol. 98, No. 23, pp. 13231-13236, Nov. 6, 2001.
Rubenstein, D., et al., "Advances in the Treatment of Virus Diseases," Practitioner, 207 (240): pp. 510-515 (Oct. 1971).
Salmon, P., et al., "Pharmacokinetics and Pharmacodynamics of Recombinant Human Interferon-β in Healthy Male Volunteers," Journal of Interferon and Cytokine Research, vol. 16, pp. 759-764 (1996).
Sharf, R., et al., "Functional Domain Analysis of Interferon Consensus Sequence Binding Protein (ICSBP) and Its Association with Interferon Regulatory Factors," The Journal of Biological Chemistry, vol. 270, No. 22, pp. 13063-13069, Jun. 2, 1995.
Smith, G., et al., "Production of Human Beta Interferon in Insect Cells Infected with a Baculovirus Expression Vector," Molecular and Cellular Biology, vol. 3, No. 12, pp. 2156-2165 (Dec. 1983).
Tan, Y., et al., "The Linkage of Genes for the Human Interferon-Induced Antiviral Protein and Indophenol Oxidase-B Traits to Chromosome G-21," Journal of Experimental Medicine, vol. 137, pp. 317-330 (1973).
Terlizzese, M., et al., "In Vitro Comparison of Inhibiting Ability of Soluble TNF Receptor p75 (TBP II) vs. Soluble TNF Receptor p 55 (TBP I) Against TNF-α and TNF-β," Journal of Interferon and Cytokine Research, vol. 16, No. 12, pp. 1047-1053 (1996).
Utsumi, J., et al., "Characterization of *E. coli*-Derived Recombinant Human Interferon-β as Compared with Fibroblast Human Interferon-β," J. Biochem., vol. 101, No. 5, pp. 1199-1208 (1987).
Uze, G., et al., "Genetic Transfer of a Functional Human Interferon α Receptor into Mouse Cells: Cloning and Expression of Its cDNA," Cell, vol. 60, pp. 225-234, Jan. 26, 1990.
Weismann, et al., "Structure and Expression of Human Alpha-Interferon Genes," Princess Takamatsu Symp., vol. 12, pp. 1-22 (1982).
Yan, H., et al., "Molecular Characterization of an Alpha Interferon Receptor 1 Subunit (IFNaR1) Domain Required for TYK2 Binding and Signal Transduction," Molecular and Cellular Biology, vol. 16, No. 5, pp. 2074-2082 (May 1996).
Yang, C., et al., "Direct Association of STAT3 with IFNAR-1 Chain of the Human Type I Interferon Receptor," The Journal of Biological Chemistry, vol. 271, No. 14., pp. 8057-8061, Apr. 5, 1996.
Alan, R., et al., "Interferon αβ Selectively Antagoinises Down-regulation of Mannosyl-Fucosyl Receptors on Activated Macrophages by Intefferon 1," Biochem. Biphys. Res. Commun., vol. 136, No. 2, pp. 737-744 (Apr. 1986).
International Search Report of PCT/IL02/01059 dated Jun. 13, 2003.
International Preliminary Report on Patentability of PCT/IL02/01059 dated Oct. 30, 2003.
Peleg-Shulman, T., et al., "Optimizing the Binding Affinity of a Carrier Protein, " The Journal of Biological Chemistry, vol. 279, No. 17, pp. 18046-18053 (2004).

* cited by examiner

MASYDSPDYTDESCTFKISLRNFRSILSWELKNHSIVPTHYTLLYTIMSK 50
PEDLKVVKNCANTTRSFCDLTDEWRSTHEAYVTVLEGFSGNTTLFSCSHN 100
                              *
FWLAIDMSFEPPEFEIVGFTNHINVMVKFPSIVEEELQFDLSLVIEEQSE 150
GIVKKHKPEIKGNMSGNFTYIIDKLIPNTNYCVSVYLEHSDEQAVIKSPL 200
KCTLLPPGQESEFSZ

Figure 2

IFNAR2 MUTANTS, THEIR PRODUCTION AND USE

CROSS-REFERENCE TO RELATED APPLICATIONS

This application is the National Stage of PCT/IL02/01059, filed Dec. 31, 2002, which claims priority to Israel Patent Application 147414, filed Dec. 31, 2001.

FIELD OF THE INVENTION

The present invention relates to mutant polypeptides of the beta chain of the type I IFN receptor (MIFNAR2) with enhanced affinity for interferon-β as compared to the wild type protein for prolonging the effect of IFNβ in vivo.

BACKGROUND OF THE INVENTION

Interferons are classified either as the leukocyte and fibroblast derived Type I interferons, or as the mitogen induced or "immune" Type II interferons (Pestka et al, 1987). Through analysis of sequence identities and common biological activities, type I interferons include interferon alpha (IFNα), interferon beta (IFNβ) and interferon omega (IFNω), while type II interferon includes interferon gamma (IFNγ).

The IFNα, IFNβ and IFNω genes are clustered on the short arm 25 of chromosome 9 (Lengyl, 1982). There are at least 25 non-allelic IFNα genes, 6 non-allelic IFNω genes and a single IFNβ gene. All are believed to have evolved from a single common ancestral gene. Within species, IFNα genes share at least 80% sequence identity with each other. The IFNβ gene shares approximately 50% sequence identity with IFNα; and the IFNω gene shares 70% homology with IFNα (Weissman et al, 1986; Dron et al, 1992). IFNα has a molecular weight range of 17-23 kDa (165-166 amino acids), IFNβ, about 23 kDa (166 amino acids) and IFNω, about 24 kDa (172 amino acids).

Type I interferons are pleiotropic cytokines having activity such as host defense against viral and parasitic infections, anti-cancer properties and as immune modulators (Baron et al, 1994; Baron et al, 1991). Type I interferon physiological responses include anti-proliferative activity on normal and transformed cells, stimulation of cytotoxic activity in lymphocytes, natural killer cells and phagocytic cells, modulation of cellular differentiation, stimulation of expression of class I MHC antigens, inhibition of class II MHC, and modulation of a variety of cell surface receptors. Under normal physiological conditions, IFNα and IFNβ (IFNα/β) are secreted constitutively by most human cells at low levels with expression being up-regulated by addition of a variety of inducers, comprising infectious agents (viruses, bacteria, mycoplasma and protozoa), dsRNA, and cytokines (M-CSF, IL-1α, IL-2, TNFα). The actions of Type I interferon in vivo can be monitored using the surrogate markers, neopterin, 2',5' oligoadenylate synthetase, and β2 microglobulin (Alam et al, 1997; Fierlbeck et al, 1996; Salmon et al, 1996).

Type I interferons (IFNα/β/ω) act through a cell surface receptor complex to induce specific biologic effects, such as anti-viral, anti-tumor, and immune modulators. The type I IFN receptor (IFNAR) is a hetero-multimeric receptor complex composed of at least two different polypeptide chains (Colamonici et al, 1992; Colamonici et al, 1993; Platanias et al, 1993). The genes coding for these chains are found on chromosome 21, and their proteins are expressed on the surface of most cells (Tan et al, 1973). The receptor chains were originally designated alpha and beta and have been renamed IFNAR1 for the alpha subunit and IFNAR2 for the beta subunit. In most cells, IFNAR1 (alpha chain, Uze subunit) (Uze et al, 1990) has a molecular weight of 100-130 kDa, while IFNAR2 (beta chain, $\beta_L$, IFNα/βR) has a molecular weight of 100 kDa. In certain cell types (monocytic cell lines and normal bone marrow cells) an alternate receptor complex has been identified, where the IFNAR2 subunit ($\beta_S$) is expressed as a truncated receptor with a molecular weight of 51 kDa. The IFNAR1 and IFNAR2 $\beta_S$ and $\beta_L$ subunits have been cloned (Novick et al, 1994; Domanski et al, 1995). The IFNAR2 $\beta_S$ and $\beta_L$ subunits have identical extracellular and transmembrane domains; however, in the cytoplasmic domain they only share identity in the first 15 amino acids. The IFNAR2 subunit alone is able to bind IFNα/β, while the IFNAR1 subunit is unable to bind IFNα/β. When the human IFNAR1 receptor subunit alone was transfected into murine L-929 fibroblasts, no human IFNαs except IFNα8/IFNαB were able to bind to the cells (Uze et al, 1990). The human IFNAR2 subunit, transfected into L cells in the absence of the human IFNAR1 subunit, bind human IFNα, binding with a Kd of approximately 0.45 nM. When human IFNAR2 subunits were transfected in the presence of the human IFNAR1 subunit, high affinity binding could be shown with a Kd of 0.026-0.114 nM (Novick et al, 1994; Domanski et al, 1995). It is estimated that from 500-20,000 high affinity and 2,000-100,000 low affinity IFN binding sites exist on most cells. Although the IFNAR1/2 complex ($\alpha/\beta_s$ or $\alpha/\beta_L$) subunits bind IFNα with high affinity, only the $\alpha/\beta_L$ pair appears to be a functional signaling receptor.

Transfection of the IFNAR1 and the IFNAR2 $\beta_L$ subunits into mouse L-929 cells, followed by incubation with IFNα2, induces an anti-viral state, initiates intracellular protein phosphorylation, and causes the activation of intracellular kinases (Jak1 and Tyk2) and transcription factors (STAT 1, 2, and 3) (Novick et al, 1994; Domanski et al, 1995). In a corresponding experiment, transfection of the IFNAR2 βs subunit was unable to initiate a similar response. Thus, the IFNAR2 $\beta_L$ subunit is required for functional activity (anti-viral response) with maximal induction occurring in association with the IFNAR1 subunit.

In addition to membrane bound cell surface IFNAR forms, a soluble IFNAR has been identified in both human urine and serum (Novick et al, 1994; Novick et al, 1995; Novick et al, 1992; Lutfalla et al, 1995). The soluble IFNAR isolated from serum has an apparent molecular weight of 55 kDa on SDS-PAGE, while the soluble IFNAR from urine has an apparent molecular weight of 40-45 kDa (p40). Transcripts for the soluble p40 IFNAR2 are present at the mRNA level and encompass almost the entire extracellular domain of the IFNAR2 subunit with two additional amino acids at the carboxy terminal end. There are five potential glycosylation sites on the soluble IFNAR2 receptor. The soluble p40 IFNAR2 has been shown to bind IFNα2 and IFNβ and to inhibit in vitro the anti-viral activity of a mixture of IFNα species ("leukocyte IFN") and individual Type I IFNs (Novick et al, 1995). A recombinant IFNAR2 subunit Ig fusion protein was shown to inhibit the binding of a variety of Type I IFN species (IFNαA, IFNαB, IFNαD, IFNβ, IFNαCon1 and IFNω) to Daudi cells and $\alpha/\beta_S$ subunit double transfected COS cells.

Type I IFN signaling pathways have been identified (Platanias et al, 1996; Yan et al., 1996; Qureshi et al., 1996; Duncan et al., 1996; Sharf et al, 1995; Yang et al, 1996). Initial events leading to signaling are thought to occur by the binding of IFNα/β/ω to the IFNAR2 subunit, followed by the IFNAR1 subunit associating to form an IFNAR1/2 complex (Platanias et al., 1994). The binding of IFNα/β/ω to the IFNAR1/2 complex results in the activation of two Janus kinases (Jak1 and Tyk2), which are believed to phosphorylate specific tyrosines on the IFNAR1 and IFNAR2 subunits. Once these subunits are phosphorylated, STAT molecules (STAT 1, 2 and 3) are phosphorylated, which results in dimerization of STAT transcription complexes followed by nuclear localization of the transcription complex and the activation of specific IFN inducible genes.

A randomized, double-blinded, placebo-controlled, two-year multicenter study demonstrated that natural human fibroblast interferon (interferon beta) administered intrathecally (IT) is effective in reducing the exacerbations of exacerbating-remitting multiple sclerosis (MS). The mean reduction in exacerbation rate of 34 patients with MS who received interferon beta administered IT was significantly greater during the study than that of 35 control patients who received placebo (Jacobs et al. 1987).

The pharmacokinetics and pharmacodynamics of Type I IFNs have been assessed in humans (Alan et al, 1997; Fierlbeck et al, 1996; Salmon et al, 1996). The clearance of IFNβ is fairly rapid with the bioavailability of IFNβ lower than expected for most cytokines. Although the pharmacodynamics of IFNβ has been assessed in humans, no clear correlation has been established between the bioavailability of IFNβ and clinical efficacy. In normal healthy human volunteers, administration of a single intravenous (iv) bolus dose (6 MIU) of recombinant CHO derived IFNβ resulted in a rapid distribution phase of 5 minutes and a terminal half-life of about 5 hours (Alam et al, 1997). Following subcutaneous (sc) or intramuscular (im) administration of IFNβ, serum levels are flat with only about 15% of the dose systemically available. The pharmacodynamics of IFNβ following iv, im or sc administration (as measured by changes in 2'5'/-oligoadenylate synthetase (2',5'-AS) activity in PBMCs) were elevated within the first 24 hours and slowly decreased to baseline levels over the next 4 days. The magnitude and duration of the biologic effect was the same regardless of the route of administration.

A multiple dose pharmacodynamic study of IFNβ has been conducted in human melanoma patients (Fierlbeck et al, 1996) with IFNβ being administered by sc route, three times per week at 3 MIU/dose over a six-month period. The pharmacodynamic markers, 2',5'-AS synthetase, $\beta_2$-microglobulin, neopterin, and NK cell activation peaked by the second injection (day 4) and dropped off by 28 days, remaining only slightly elevated out to six months.

Purification and refolding of the extracellular part of human IFNAR2 (IFNAR2-EC) expressed in *Escherichia coli* and its characterization with respect to its interaction with interferon alpha2 (IFNα2) has been reported (Piehler and Schreiber 199A). The 25 kDa, non-glycosylated IFNAR2-EC was shown to be a stable, fully active protein, which inhibits antiviral activity of IFNα2. The stoichiometry of binding IFNα2 is 1:1, as determined by gel filtration, chemical cross-linking and solid-phase detection. The affinity of this interaction was found to be about 3 nM (Piehler and Schreiber 2001). The rate of complex formation is relatively high compared to other cytokine-receptor interactions. The salt dependence of the association kinetics suggests a limited but significant contribution of electrostatic forces towards the rate of complex formation. The dissociation constant increases with decreasing pH according to the protonation of a base with a pKa of 6.7. The affinity of IFNβ to IFNAR2 is about two-fold higher than that of IFNα2 to IFNAR2 (Piehler and Schreiber 1999B).

Single mutations in the binding site of IFNAR2 allowed mapping of differences in binding of IFα2 and IFNβ (Piehler and Schreiber 1999B). For example, a mutation H78A was found to stabilize the complex with IFNβ nearly by two fold, while destabilized the complex with IFα2 more than two fold. A mutation N100A was found to hardly affect the rates for binding IFα2, whereas it decreased the dissociation rate constant for IFNβ by almost four fold.

EP1037658 discloses that the in vivo effect of Type I interferon (IFN) can be prolonged by administering the interferon in the form of a complex with an IFN binding chain of the human interferon alpha/beta receptor (IFNAR) i.e. IFNAR behaves as a carrier protein for IFN. Such a complex also improves the stability of the IFN and enhances the potency of the IFN. The complex may be a non-covalent complex or one in which the IFN and the IFNAR are bound by a covalent bond or a peptide. EP1037658 also discloses that storing IFN in the form of such a complex improves the storage life of the IFN and permits storage under milder conditions than would otherwise be possible.

There exists a need for an IFNAR2 with improved affinity towards IFNβ, but not to IFNα2, making IFNAR2 a better and specific carrier for IFNβ.

SUMMARY OF THE INVENTION

The invention provides an IFNAR2 mutant polypeptide (MIFNAR2) mutated at amino acid residues histidine 78 and asparagine 100, having higher affinity for interferon-β (IFNβ) than the wild type polypeptide, or an analog, functional derivative, fusion protein or salt thereof. The mutations are substitutions of amino acids, preferable conservative amino acids, more preferable alanine, aspartic acid or histidine. The IFNAR2 mutant has about 25, preferably 50 and more preferably 100-fold higher affinity than the wild type protein and a preferred Kd of about 30 pM.

More particularly the invention provides an IFNAR2 mutant polypeptide fragment comprising the extracellular domain.

In addition the invention provides a DNA encoding the IFNAR2 mutant polypeptide of the invention, a vector comprising said DNA, host cells comprising said vector and methods for producing a polypeptide mutant of the invention by cultivating said host cells and isolating the produced polypeptide mutant.

In another aspect the invention provides the use of an IFNAR2 mutant polypeptide for the manufacture of a medicament for modulating the effects of IFN, preferably IFNβ, in vivo.

The invention also provides a pharmaceutical composition comprising a therapeutically effective amount of an IFNAR2 mutant or its extracellular domain fragment, to be administrated alone or co-administrated with IFN, more preferably IFNβ, separately or covalently bound. More specifically the invention provides pharmaceutical compositions for augmenting the anti-viral, anti-cancer and immune modulating properties of IFNβ and for treatment of autoimmune diseases, such as multiple sclerosis, rheumatoid arthritis, myasthenia gravis, diabetes, ulcerative colitis and lupus.

Furthermore, the invention provides methods of treatment of autoimmune diseases, viral disease and cancer, comprising administration of an IFNAR2 mutant polypeptide of the invention.

In addition the invention provides the use of IFNAR2 mutant polypeptide, preferably co-administered with an IFN antagonist, for inhibition of IFN activity in a disease which is aggravated or caused by IFN.

The invention also provides the use of the IFNAR2 mutant polypeptide of the invention in a formulation to prevent IFN oligomerization.

BRIEF DESCRIPTION OF THE FIGURES

FIG. 2 shows the amino acid sequence of the extracellular domain of the IFNAR2 protein (not including the leader sequence) (SEQ ID NO: 1) and the mutated amino acid residues (marked with an asterisk).

DETAILED DESCRIPTION OF THE INVENTION

The invention relates to a mutant of the beta chain of the type I IFN receptor (IFNAR2), mutated at amino acid residues H78 and N100 (see DNA sequence of wild type IFNAR2 in FIG. 2, SEQ ID N: 1) having increased affinity to IFNβ, but not to IFNα2 (MIFNAR2). The invention relates also to a drug carrier system to enhance activity of IFN comprising the extracellular domain (EC) of MIFNAR2. The invention relates to MIFNAR2, or an analog, functional derivative, fusion protein, fragment thereof or salts thereof.

Carriers are usually administered to prolong the intra-vascular retention time of proteins having molecular weight below 50,000 daltons (e.g., interferon). Particularly beneficial are such carriers that bind non-covalently and permit constant release of the drug. Using such a carrier is desirable in order to have at any time some portion of the free drug available for curative activity (about 20%) and some amount of drug bound to the carrier and protected (about 80%).

Figure 1:
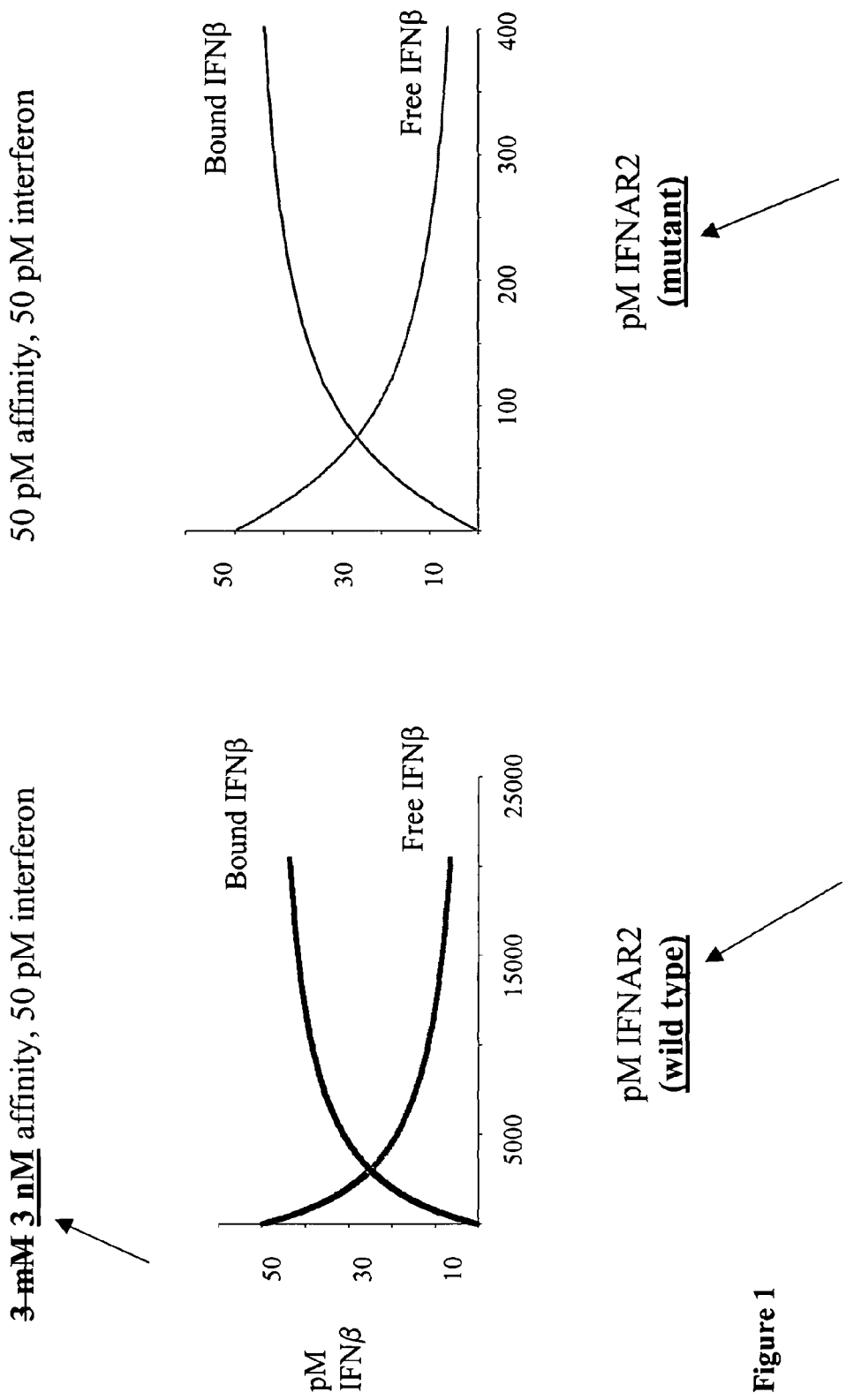
FIG. 1 depicts a simulation of the concentrations of bound and free IFNβ using a constant concentration of IFN (50 pM) and increasing concentrations of wild type IFNAR2 EC (left) and mutant IFNAR2 EC (right), with a Kd of 3 nM and 50 pM, respectively, calculated in accordance with the law of mass action.

FIG. 1 (left panel) depicts a simulation of the concentration of bound and free IFNβ in the presence of different concentrations of IFNAR2 based on the law of mass action and on a Kd of 3 nM (tested by reflectometric interference spectroscopy [RifS]). This simulation shows that in order to achieve 20% of free IFNβ (10 pM, which equals about 100 Units), and 80% bound, a very high concentration of IFNAR2 protein such as 12.5 nM (which is equivalent to 300 μg/Kg of non-glycosylated IFNAR2) is needed.

Thus, using an IFNAR2 mutant with 50 fold and higher affinities to IFNβ as a carrier (see simulation FIG. 1, right panel), would be advantageous since with such a mutant theoretically only about 0.24 nM will be required to get 20% IFNβ free (which is equivalent to 6 μg/Kg).

Figure 3:
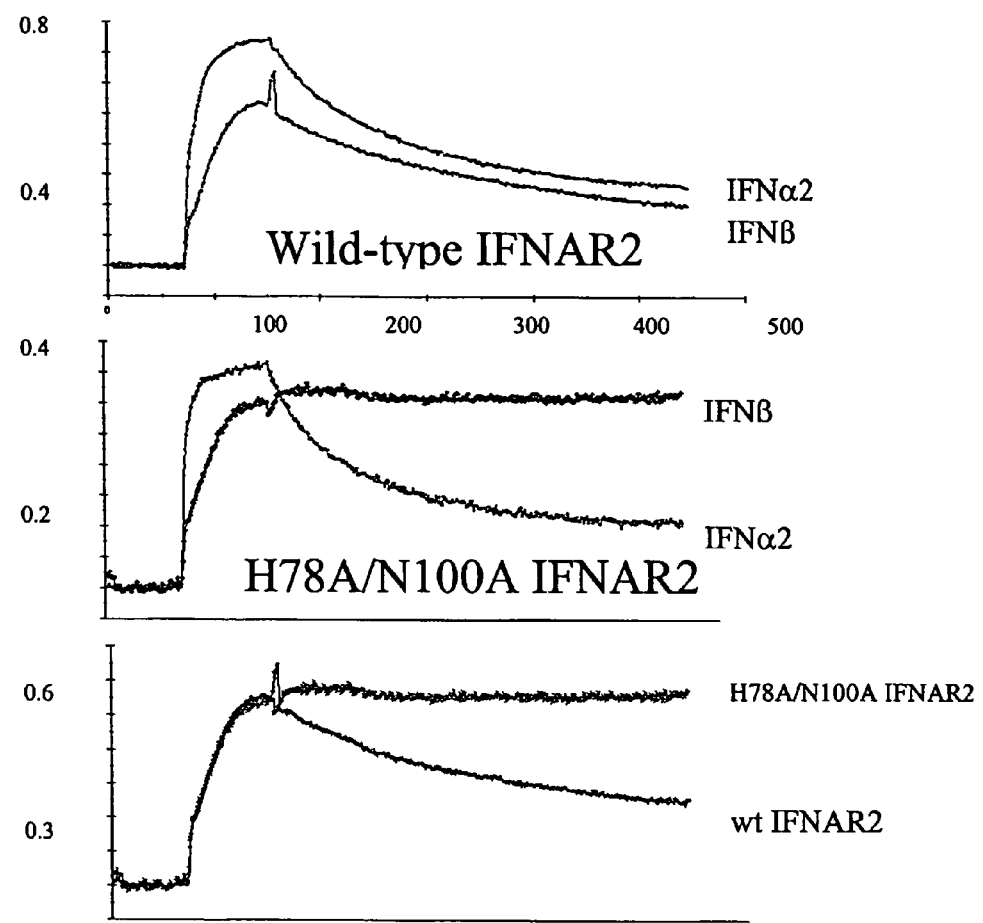
FIG. 3 shows the binding of IFNβ and IFNα2 to the IFNAR2 EC H78A/N100A mutant. Association and disassociation of IFNβ and IFNα2 to the wild type IFNAR2 EC (upper panel), to the IFNAR2 EC H78A/N100A mutant (middle panel) and the binding of the wild type and mutant IFNAR2 EC H78A/N100A mutant to IFNβ (lower panel) was measured using reflectometric interference spectroscopy (RifS), with IFNAR2 immobilized to the surface (described in Piehler and Schreiber 2001). Y-axis=signal (nanometer) and the X-axis=time (seconds).
Figure 4:
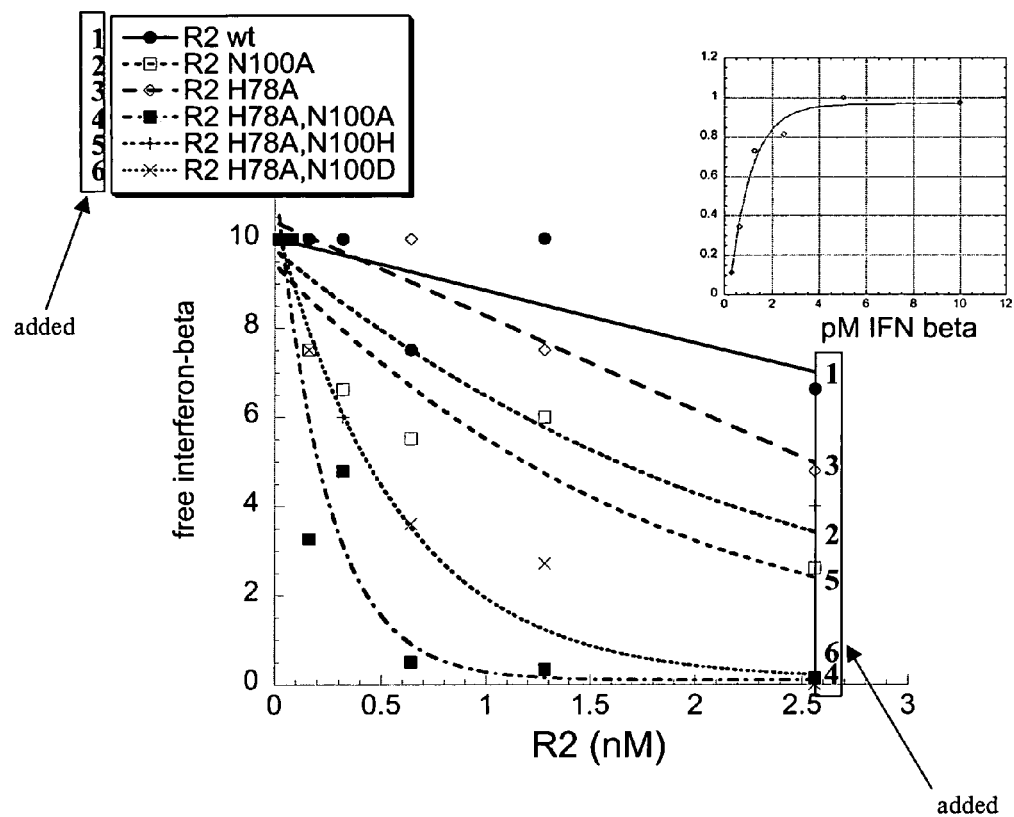
FIG. 4 shows occlusion of IFNβ by IFNAR2 wild type and mutants. A constant amount of IFNβ (10 pM) was mixed with different concentrations of IFNAR2 (R2) wild type and mutants (single mutants R2N100A and R2H78A, double mutants R2 H78A/N100A, R2 H78A/N100H and R2 H78A/N100D), and the residual antiviral activity at equilibrium was determined in WISH cells. In the upper box, a plot of the antiviral activity of IFNβ as a function of its concentration in the absence of IFNAR2 is shown (Y-axis=survival index). This plot is used as a standard to determine how much of the IFNβ is free (active) in the anti-viral assay.

A mutant of the IFNAR2 with increased affinity to IFN (MIFNAR2) was generated. To get MIFNAR2 EC, the wild type IFNAR2 EC (FIG. 1, SEQ ID NO: 1) was mutated at two amino acid residues, residue 78 histidine and residue 100 asparagine (see FIGS. 2, 3 and 4, SEQ ID NOs: 2, 3, and 4). This mutant IFNAR2 EC proteins turned out to be a better carrier specifically for IFNβ, i.e., has improved affinity for IFNβ while its affinity towards IFNα2 remains unchanged. The affinity of the mutants for IFNβ was found to be 26, 40 and above 50 fold higher than that of the wild type (Table 4). The results obtained show that despite the increased affinity of this mutated soluble receptor (Kd of the H78A/N100A IFNAR2 mutant ~30 pM versus Kd of WT protein=3 nM), enough IFNβ remains unbound and therapeutically active, as evidenced by the anti-viral protective activity of VSV challenged WISH cells (FIG. 4). The results show also that the levels of IFN occlusion (bound IFN at equilibrium conditions) obtainable with wild type IFNAR2 EC could be accomplished using lower concentrations of IFNAR EC mutants. The best results are obtained with mutants modified in both residues, particularly when both amino acids are mutated to alanine, H78A/N100A IFNAR2, e.g., in order to get 80% of IFNβ bound (8 pM occluded and 2 pM free IFNβ) about 30 fold less H78A/N100A IFNAR mutant is required over the wild type IFNAR2 protein.

These results show that the double mutated IFNAR2 occludes more effectively IFNβ and administration of considerably lower amounts is required to fulfill its carrier activity towards IFNβ.

The advantages of using MIFNAR2 EC are that (I) it is possible to administer lower quantities (thus technically feasible) of the receptor as a carrier (II) because of the stabilizing activity of the mutant it is possible to reduce the amount of IFNβ administrated, and consequently to reduce some of the unwanted side effects of interferon treatment (III) the increase in the activity by the mutant is specific to IFNβ and (IV) that in some inflammatory disorders, where it may be required to lower the IFN concentrations, it is possible under certain conditions to use this mutant as an effective antagonist specifically towards IFNβ, but not IFNα2.

MIFNAR2-EC may be administered alone to stabilize and enhance the activity of endogenous IFNβ. This is particularly useful for the treatment of patients having a disease or condition which naturally causes the elevation of native IFN, so that the IFN will already be circulating in the body for its intended natural effect of fighting such disease or condition. MIFNAR2-EC will act specifically on endogenous IFNβ, but less towards IFNα2. Alternatively, MIFNAR2-EC may be co-administrated together with IFN, preferably IFNβ or may be administrated covalently bound to IFNβ, i.e., as a complex, to modulate the activity of IFNβ. Preferably, MIFNAR2 and IFNβ used to generate the complex are recombinant molecules.

The technology required to produce the fusion protein of the mutant EC IFNAR2 and IFN is similar to the technology described for wild type IFNAR/IFN complex production which is described in detail in WO9932141, wherein the IFNAR2 mutated at H78 and N100 (MIFNAR2) is used instead of the wild type version.

The implications of using a MIFNAR2/IFNβ non-covalently bound complex according to the invention are that lower concentrations of IFNAR2 EC are required and may be used for a variety of therapeutic indications in which IFN by itself is therapeutically active.

These indications include those in which free IFNs have shown some therapeutic activity, such as anti-viral, anti-cancer and immune modulatory activity. It is expected that the mutant IFNAR2/IFN complex, by virtue of its greater potency, enhanced activity and/or improved pharmacokinetics (i.e. half-life), will be more efficacious in treating viral, oncologic and autoimmune disorders.

When administered in vivo the interferon receptor complex enhances the bioavailability, pharmacokinetics, and/or pharmacodynamics of the IFN, thus augmenting the anti-viral, anti-cancer and immune modulating properties of the IFN. The preferred molecules for use in the complexes of the present invention comprise the amino acid sequence of native IFNβ and MIFNAR2 (SEQ ID NOs: 2, 3, and 4). The native sequence is that of a naturally occurring human IFNβ. Such sequences are known and can be readily found in the literature. Naturally occurring allelic variations are also considered to be native sequences.

The present invention also includes analogs of the above MIFNAR2 EC. Such analogs may be ones in which up to about 30, preferably up to 20 and most preferably 10 amino acid residues may be deleted, added or substituted by others in the proteins, except mutations at residues 78 and 100 which results in a decrease in the affinity of MIFNAR2 for IFNβ to the wild type IFNAR2 affinity for IFNβ. These analogs are prepared by known synthesis and/or by site-directed mutagenesis techniques or any other known technique suitable therefore.

Any such analog preferably has a sequence of amino acids sufficiently duplicative of that of the basic MIFNAR2 such as to have substantially similar activity thereto. Thus, it can be determined whether any given analog has substantially the same activity and/or stability as the protein and complex of the invention by means of routine experimentation, comprising subjecting each such analog to binding and biological activity tests. MIFNAR2 EC analogs may bind IFNβ with at least 15 fold and about 50 to 100 fold higher affinity over the wild type protein wherein the affinity towards IFNα2 is not significantly changed. The MIFNAR2 EC analogs may exhibit a Kd of about 30 pM and lower towards IFNβ. The binding tests for MIFNAR2 and IFN interaction may involve analytical gel filtration, optical heterogeneous phase detection (such as surface plasmon resonance [SPR], or reflectometric interference spectroscopy [RifS] which resembles the widely used BIACORE technique) and fluorescent spectroscopy (Piehler and Schreiber 1999A Piheler and Schreiber 2001).

Analogs of the complex which can be used in accordance with the present invention, or nucleic acid sequence coding therefore, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz et al, Principles of Protein Structure, Springer Verlag, New York (1978); and Creighton, T. E., Proteins: Structure and Molecular Properties, W.H. Freeman & Co, San Francisco (1983), which are hereby incorporated by reference.

For a presentation of nucleotide sequence substitutions, such as codon preferences, see Ausubel et al (1987, 1992), A.1. I-A. 1.24, and Sambrook et al (1987, 1992), 6.3 and 6.4, at Appendices C and D.

Preferred changes for analogs in accordance with the present invention are what are known as "conservative" substitutions. Conservative amino acid substitutions of those in the sequence of the proteins in the invention may include synonymous amino acids within a group, which have sufficient similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues (Anfinsen, 1973). Analogs produced by such deletions and or insertions come within the purview of the present invention. Preferably, the synonymous amino acid groups are those defined in Table I. More preferably, the synonymous amino acid groups are those defined in Table II; and most preferably the synonymous amino acid groups are those defined in Table III.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining analogs of MIFNAR2 or MIFNAR2 EC for use in the present invention include any known method steps, such as presented in U.S. Pat. Nos. RE 33,653; 4,959,314; 4,588,585 and 4,737,462, to Mark et al; U.S. Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al).

The term “essentially corresponding to” is intended to comprehend analogs with minor changes to the sequence of the basic MIFNAR2 or MIFNAR2 EC which do not affect the basic characteristics thereof, e.g., its specific enhanced binding and affinity to IFNβ. The type of changes which are generally considered to fall within the “essentially corresponding to” language are those which would result from conventional mutagenesis techniques of the DNA encoding the complex of the invention, resulting in a few minor modifications, and screening for the desired activity in the manner discussed above.

Preferably, the MIFNAR2 portion of the complex will have a core sequence which is the same as that of the native sequence or biologically active fragment thereof, or a variant thereof which has an amino acid sequence having at least 70% identity to the native amino acid sequence and retains the biological activity thereof. More preferably, such a sequence has at least 85% identity, at least 90% identity, or most preferably at least 95% identity to the native sequence.

With respect to the IFN portion of the complex, the core sequence which may be used is the native sequence, or a biologically active fragment thereof, or a variant thereof which has an amino acid sequence having at least 70% identity thereto, more preferably, at least 85% or at least 90% identity, and most preferably at least 95% identity. Such analogs must retain the biological activity of the native IFN sequence or fragment thereof, or have antagonist activity as discussed herein below.

The term “sequence identity” as used herein means that the sequences are compared as follows. The sequences are aligned using Version 9 of the Genetic Computing Group’s GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Analogs in accordance with the present invention may also be determined in accordance with the following procedure. With respect to either the MIFNAR2 portion of the complex or the IFN portion of the complex, the DNA of the IFNAR and IFN sequence are known to the prior art and is either found in the literature cited in the background section of the present specification or can be readily located by those of ordinary skill in the art. Polypeptides encoded by any nucleic acid, such as DNA or RNA, which hybridizes to the complement of the native DNA or RNA under highly stringent or moderately stringent conditions, as long as that polypeptide maintains the biological activity of the native sequence or, in the case of IFN, either maintains the biological activity of MIFNAR2 or MIFNAR2 EC or possesses antagonistic activity, are also considered to be within the scope of the present invention.

“Stringent conditions” refers to hybridization and subsequent washing conditions, which those of ordinary skill in the art conventionally refer to as “stringent”. See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

“Functional derivatives” as used herein covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of the corresponding protein of the complex as described herein and do not confer toxic properties on compositions containing it or the complex made therefore. Derivatives may have chemical moieties, such as carbohydrate or phosphate residues, provided such a fraction has the same biological activity and remains pharmaceutically acceptable.

For example, derivatives may include aliphatic esters of the carboxyl of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains, which may mask antigenic sites and extend the residence of the complex or the portions thereof in body fluids.

The term “fused protein” refers to a polypeptide comprising an MIFNAR2, or MIFNAR2 EC or an analog or fragment thereof, fused with another protein, which, e.g., has an extended residence time in body fluids. An MIFNAR2 or MIFNAR2 EC may thus be fused to another protein, polypeptide or the like, e.g., an immunoglobulin or a fragment thereof.

A "fragment" according to the present invention may, e.g., be a fragment of MIFNAR2 or MIFNAR2 EC. The term fragment refers to any subset of the molecule, that is, a shorter peptide that retains the desired biological activity. Fragments may readily be prepared by removing amino acids from either end of the MIFNAR2 molecule and testing the resultant fragment for its properties to bind to IFNβ. Proteases can be used for removing one amino acid at a time from either the N-terminal or the C-terminal of a polypeptide, and so determining fragments, which retain the desired biological activity, involves only routine experimentation.

As active fragments of an MIFNAR2, analogs and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fragment has substantially similar activity.

The term "salts" herein refers to both salts of carboxyl groups and to acid addition salts of amino groups of the complex of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must have substantially similar biological activity to the complex of the invention or its analogs.

The term "biological activity" as used herein is interpreted as follows. Insofar as the MIFNAR2 is concerned, the important biological activity is its ability to bind to IFNβ with increased affinity. Thus, analogs or variants, salts and functional derivatives must be those chosen so as to maintain this interferon-binding ability. This can be tested by routine binding assay experiments. In addition, fragments of the MIFNAR2, or analogs thereof, can also be used as long as they retain their interferon-enhanced binding activity. Fragments may readily be prepared by removing amino acids from either end of the interferon-binding polypeptide and testing the resultant for interferon-binding properties.

Additionally, the polypeptide which has such interferon-binding activity, be it MIFNAR2, MINFAR2 EC, an analog, functional derivative, or fragment, can also contain additional amino acid residues flanking the interferon-binding polypeptide. As long as the resultant molecule retains the increased interferon-binding ability of the core polypeptide, one can determine whether any such flanking residues affect the basic and novel characteristics of the core peptide, i.e., its interferon-binding characteristics, by routine experimentation. The term "consisting essentially of", when referring to a specified sequence, means that additional flanking residues can be present which do not affect the basic and novel characteristic of the specified sequence. This term does not comprehend substitutions, deletions or additions within the specified sequence.

While MIFNAR2 or MIFNAR2 EC have been used throughout this description and in the examples, it should be understood that this is merely the preferred example and that the IFNAR1 subunit, and particularly its extracellular domain, may be used together with MIFNAR2 or MIFNAR2 EC.

With respect to the interferon part of the complex of the present invention, the biological activity which must be maintained in any analog, functional derivative, fusion protein or fragment is the activity of the interferon relied upon for the intended utility. In most instances, this will be the ability to bind to a native cell surface receptor and thereby mediate signal production by the receptor. Thus, any such analog, derivative or fragment should maintain such receptor agonist activity to be useful in the present invention for such a utility. On the other hand, it is sometimes useful to have a molecule with antagonist activity on the receptor so as to prevent the biological activity of native interferon. Such an antagonist can also be used for prolonged beneficial effect by means of the complex of the present invention. For such utilities in which it is desired to eliminate an undesired effect of interferon, analogs which are still bound by the receptor and by the IFNAR portion of the complex but which do not mediate a signal and block signal generation by the native interferon on that receptor (i.e., interferon antagonist), may also be considered to be biologically active for the purpose of this invention and to be encompassed by the term interferon when used with respect to the complexes of the present invention. Straightforward assays can determine whether any such analog maintains such receptor agonist activity or has receptor antagonist activity and would, thus, be useful for one of the utilities of the present invention.

The present invention also relates to DNA sequences encoding MIFNAR2 EC, e.g., DNA encoding the amino acid sequences in SEQ ID NOs: 2, 3 and 4 or analogs, and fragments thereof, as well as DNA vectors carrying such DNA sequences for expression in suitable prokaryotic or eukaryotic host cells.

The ability to generate large quantities of heterologous proteins using a recombinant protein expression system has led to the development of various therapeutic agents, e.g., t-PA and EPO (Edington, 1995). The various expression hosts from which recombinant proteins can be generated range from prokaryotic in origin (e.g., bacteria) (Olins, 1993), through lower eukaryotes (e.g., yeast) (Ratner, 1989) to higher eukaryotic species (e.g., insect and mammalian cells) (Reuveny, 1993; Reff, 1993). All of these systems rely upon the same principle—introducing the DNA sequence of the protein of interest into the chosen cell type (in a transient or stable fashion, as an integrated or episomal element) and using the host transcription, translation and transportation machinery to over-express the introduced DNA sequence as a heterologous protein (Keown, 1990).

Various protocols for the production of recombinant heterologous proteins are described (Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989).

In addition to the expression of native gene sequences, the ability to manipulate DNA at the nucleotide level has expedited the development of novel engineered sequences which, although based on natural proteins, possess novel activities as a result of the alteration in primary protein structure (Grazia, 1997).

Moreover, chosen sequences of DNA can be physically linked to generate transcripts which develop into novel fusion proteins where once independent proteins are now expressed as one polypeptide unit (Ibanez, 1991). The activity of such fusion proteins can be different, e.g., more potent, than either of the individual proteins (Curtis, 1991).

For co-administration of MIFNAR2 EC with IFN, human IFNβ may be derived from a production process, which uses the mammalian Chinese hamster ovary cell (CHO) as disclosed in EP220574. Type 1 interferons can be expressed in a variety of host cells including those of bacteria (Utsumi, 1987), insect (Smith, 1983) and human (Christofinis, 1981) origin. Also human MIFNAR2 or a fragment thereof may be expressed using the CHO host cell. For secretion of MIFNAR2 EC from CHO cells, MIFNAR2 EC DNA sequence may be ligated to the sequence of the human growth hormone signal peptide as described in the patent application WO0022146. Alternatively, soluble receptors, such as MIFNAR2 EC, may be expressed successfully in bacterial expression systems (Terlizzese, 1996).

The invention also relates to a pharmaceutical composition comprising as active ingredient an MIFNAR2, MIFNAR2 EC, MIFNAR2 EC/IFN complex or analogs, fusion proteins, functional derivatives, fragments thereof or mixtures thereof or salts thereof and a pharmaceutical acceptable carrier, diluent or excipient. An embodiment of the pharmaceutical composition of the invention includes a pharmaceutical composition for enhanced IFN type action, in the treatment of viral diseases, in anti-cancer therapy, in immune modulation therapy, e.g., in autoimmune diseases and other applications of interferons and cytokines related thereto.

The pharmaceutical compositions of the invention are prepared for administration by mixing an MIFNAR2, MIFNAR2 EC, MIFNAR2 EC/IFN complex or analogs, fusion proteins, functional derivatives, fragments thereof or mixtures thereof or salts thereof with physiologically acceptable stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, and subcutaneously, by local injection or topical application, or continuously by infusion, etc. The amount of active compound to be administered will depend on the route of administration, the disease to be treated and the condition of the patient.

The invention relates to a method for treatment of autoimmune diseases such as multiple sclerosis, rheumatoid arthritis, myasthenia gravis, diabetes, lupus and ulcerative colitis, comprising administration of a therapeutically effective amount of an MIFNAR2, MIFNAR2 EC, MIFNAR2 EC/IFN complex or analogs, fusion proteins, functional derivatives, fragments thereof or mixtures thereof or salts thereof.

The invention relates to a method for treatment of a viral disease such as granulomatous disease, condyloma acuminatum, juvenile laryngeal papillomatosis, hepatitis A or chronic infection with hepatitis B and C viruses, comprising administration of a therapeutically effective amount of an MIFNAR2, MIFNAR2 EC, MIFNAR2 EC/IFN complex or analogs, fusion proteins, functional derivatives, fragments thereof or mixtures thereof or salts thereof.

The invention relates to a method for treatment of various types of cancer such as hairy cell leukemia, Kaposi's sarcoma, multiple myeloma, chronic myelogenous leukemia, non-Hodgkins's lymphoma or melanoma, comprising administration of a therapeutically effective amount of an MIFNAR2, MIFNAR2 EC, MIFNAR2 EC/IFN complex or analogs, fusion proteins, functional derivatives, fragments thereof or mixtures thereof or salts thereof.

In the above methods an MIFNAR2, MIFNAR2 EC, MIFNAR2 EC/IFN complex or analogs, fusion proteins, functional derivatives, fragments thereof or mixtures thereof or salts thereof may be administered together with IFN, preferably IFNβ.

A "therapeutically effective amount" is such that when administered, an MIFNAR2, MIFNAR2 EC, MIFNAR2 EC/IFN complex or analogs, fusion proteins, functional derivatives, fragments thereof or mixtures thereof or salts thereof results in modulation of the biological activity of IFNβ. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the activity of an MIFNAR2, MIFNAR2 EC, MIFNAR2 EC/IFN complex or analogs, fusion proteins, functional derivatives, fragments thereof or mixtures thereof or salts thereof.

Local injection, for instance, will require a lower amount of the protein on a body weight basis than will intravenous infusion.

Free IFNβ has a tendency to oligomerize. To suppress this tendency, present day formulations of IFNβ have an acidic pH, which may cause some localized irritation when administered. As an MIFNAR2, MIFNAR2 EC, or analogs, fusion proteins, functional derivatives, fragments thereof or mixtures thereof or salts thereof can serve as a superior stabilizer over the wild type version for IFNβ and thereby prevent oligomerization, its use in IFNβ formulations can serve to stabilize the IFNβ and thereby obviate the necessity of acidic formulations. Accordingly, a non-acidic pharmaceutical composition containing an MIFNAR2, MIFNAR2 EC, or analogs, fusion proteins, functional derivatives, fragments thereof or mixtures thereof or salts thereof, along with other conventional pharmaceutically acceptable excipients, is also a part of the present invention.

The present invention also includes uses of an MIFNAR2, MIFNAR2 EC, MIFNAR2 EC/IFN complex or analogs, fusion proteins, functional derivatives, fragments thereof or mixtures thereof or salts thereof for anti-viral, anti-cancer and immune modulation therapy. Specifically, the mutant interferon receptor and interferon complexes of this invention are useful for anti-viral therapy in such therapeutic indications as chronic granulomatous disease, condyloma acuminatum, juvenile laryngeal papillomatosis, hepatitis A and chronic infection with hepatitis B and C viruses.

In particular, the mutant interferon receptor and interferon complexes of this invention are useful for anti-cancer therapy in such therapeutic indications as hairy cell leukemia, Kaposi's sarcoma, multiple myeloma, chronic myelogenous leukemia, non-Hodgkins's lymphoma and melanoma.

The mutant interferon receptor and interferon complexes of this invention are also useful for immune modulation therapy, in autoimmune diseases, e.g., multiple sclerosis, rheumatoid arthritis, myasthenia gravis, diabetes, lupus, ulcerative colitis etc.

"An autoimmune disorder" is a disease in which a person's immune system begins to attack his or her own body. The immune system creates antibodies against its own tissues. Virtually every part of the body is susceptible to an autoimmune disorder.

The mutant interferon receptor and interferon complexes are also useful for treating neurodegenerative diseases, preferably multiple sclerosis.

The invention further relates to a pharmaceutical composition comprising an MIFNAR2, MIFNAR2 EC, MIFNAR2 EC/IFN complex or analogs, fusion proteins, functional derivatives, fragments thereof or mixtures thereof or salts thereof, to a pharmaceutical composition comprising an expression vector, in particular a lentiviral gene therapy vector expressing an, MIFNAR2, MIFNAR2 EC, MIFNAR2 EC/IFN complex or analogs, fusion proteins, fragments thereof.

The terms "treating" as used herein should be understood as preventing, inhibiting, attenuating, ameliorating or reversing any or all symptoms or cause(s) of the disease.

Having now described the invention, it will be more readily understood by reference to the following examples that are provided by way of illustration and are not intended to be limiting of the present invention.

EXAMPLES

Example 1

Protein Expression and Purification

IFNAR2-EC (extracellular domain) and IFNα was expressed in *E. coli* purified by ion exchange and size-exclusion chromatography as described (Piehler & Schreiber, 1999A). The levels of expression of IFNAR2-EC mutants were as high as the wild type. Wild type, glycosylated IFNβ was produced in CHO (disclosed in EP220574). Protein concentrations were determined from absorbance at 280 nm (Piehler & Schreiber, 1999A) with 1:280=18,070 M-1 for IFNα2, 1:280=30,050 M-1 for IFNβ and 1:280=26,500 M-1 for IFNAR2-EC (corrected to 1:280=21,100 M-1 for the tryptophan mutants of IFNAR2-EC W102A and W74F). Protein purity was analyzed by SDS-PAGE under non-reducing conditions.

Example 2

Generation of IFNAR EC Mutants

Site-directed mutagenesis was carried out by PCR with the template pT72CR2 (Piehler and Schreiber 1999) and with 18-21 nucleotide primers containing the mutated codon using high fidelity polymerases pwo (Boehringer Mannheim) and Pfu (Stratagene) as described in detail (Albeck & Schreiber, 1999). After phosphorylation and ligation, the mutated plasmids were used to transform *E. coli* TG1 cells. The sequence of the whole expressed gene containing the mutation was verified by DNA sequencing (Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989).

Mutants were generated in which two amino acid residues, histidine 78 (H78) and Asparagine 100 (N100), were mutated: A—both to alanine residues (H78A/N100A mutant), B—to alanine and aspartic acid respectively (H78A/N100D) and C—to alanine and histidine respectively (H78A/N100H).

Example 3

Thermodynamic and Kinetic Analysis

All thermodynamic and kinetic data were obtained from label-free heterogeneous phase detection. The interaction between IFNβ2 and IFNAR2-EC was monitored by reflectometric interference spectroscopy (RifS) under flow-through conditions as described (Piehler & Schreiber, 1999A). This technique is similar to Biacore and is used to accurately measure affinity of binding between two proteins. IFNAR2-EC (wild-type or mutant) was immobilized trough immobilized specific antibodies (as described by Piehler and Schreiber 2001). All measurements with IFNβ, IFNα2 and IFNAR2-EC were carried out in 50 mM Hepes with 500 mM NaCl and 0.01% Triton X100 at pH 7.4. The interaction was measured at 500 mM NaCl in order to eliminate non-specific interactions with the surface, which was observed with IFNβ at 150 mM NaCl.

Association and dissociation kinetics were measured by standard injection protocols and corrected by blank runs. Dissociation rate constants were measured at IFN concentration in the range of 1-1000 nM in order to saturate the surface. The total range of dissociation was used for fitting a 1:1 kinetic model (Piehler & Schreiber, 2001).

Example 4

Anti-Viral Activity Assay

Anti-viral activity of IFNβ was assayed as the inhibition of the cytophatic effect of vesicular stomatitis virus (VSV) on human WISH cells (Rubinstein et al., 1981).

Example 5

Measurement of IFN Binding to Mutant IFNAR2

Binding of the IFNβ and IFNα2 to the H78A/N100A mutant (example 2) was measured and compared to the wild type EC receptor by RifS (example 3). While the association rate of IFNβ to the H78A/N100A mutant was found to be similar to that of the wild type (FIG. 3) the disassociation rate was found to be significantly lower. The calculated affinity of IFNβ to H78A/N100A mutant is about 30 pM versus the affinity to the WT protein of about 3 nM. In contrast to IFNβ, both the association and disassociation rate of IFNα2 to the H78A/N100A mutant, were found to be similar to the rates obtained with the wild type protein (FIG. 3). These results show that the affinity of the IFNAR2 mutant was found to be approximately 100 times higher than the wild type towards IFNβ and unchanged towards IFNα2.

Example 6

Relative Affinities of Interferon Towards the Mutant IFNAR2

The binding and affinities of IFNAR EC receptor and mutant receptor EC (example 2) to IFNβ and IFNα2 were measured using RifS, with IFNAR2 wild type or mutant immobilized to the surface trough specific antibodies (example 3). After measuring the affinities, the relative affinities were obtained by comparing the Kd of the mutant receptor over the Kd of the wild type receptor (Table 4).

The Kd of binding of interferon to IFNAR2 extracellular domain (EC) was measured by RifS and was found to be about 3 nM (example 5). The Kd of IFNβ binding to H78A/N100A (EC) mutant was about 30 pM. The exact measurement of Kd for this mutant was not possible, because binding was to tight to get good data from RifS. The Kd of IFNα2 to the H78A/N100A EC mutant was found to be similar to the wild type receptor. The results in Table 4 show the relative affinities of the IFNAR EC mutants compared to the wild type IFNAR2 receptor EC. The mutants were the following: mutated in one amino acid residue, H78A or N100A, and mutated in two amino acids H78A/N100A, H78A/N100D and H78A/N100H, wherein the amino acid N100 is mutated into alanine, aspartic acid or histidine respectively (example 2). The results demonstrate that the single mutations in IFNAR2 increase the affinity of the complex from 4.6 up to 7.3 fold, while the double mutation causes a synergistic effect, increasing the affinity of the complex by 26 and to above 50-fold. The best mutant in terms of affinity was found to be the double mutant with the N100 modified to alanine, exhibiting over 50 fold increased affinity versus the wild type version.

TABLE 4

| IFNAR2 | IFNα2 | IFNβ |
|---|---|---|
| wt | 1.0 | 1.0 |
| H78A | 0.4 | 4.6 |
| N100A | 2.0 | 7.3 |
| H78A/N100A | 0.7 | >50 |
| H78A/N100D | 1.0 | 40.0 |
| H78A/N100H | 0.9 | 26.0 |

Example 7

Occlusion of Interferon Beta by the IFNAR2 Mutant

The capability of IFNAR2 EC wild type and mutants EC to serve as carriers of IFNβ was compared. For that purpose antiviral activity of IFNβ residual (free) in samples comprising a constant concentration of IFNβ (10 pM) mixed with varying concentrations of recombinant soluble IFNAR2 EC or IFNAR2 mutants EC (example 6) was monitored. In the antiviral assay, the mixture (IFNAR2/IFN complex) was added to WISH cells (human amniotic cells). These WISH cells were then challenged with vesicular stomatitis virus (VSV), and the residual (free) anti-viral activity of IFNβ was monitored as the degree of cell survival following 24-hour incubation (example 4). The free IFNβ present in samples having different amount of WT or mutant IFNAR2 EC (R2) concentration was determined from a survival dose curve of antiviral activity as a function of IFNβ concentration carried out in the absence of IFNAR2 (FIG. 4 upper plot).

The mutants tested were the following: IFNAR2 EC mutated in one amino acid residue, H78A or N100A, and mutated in two amino acids H78A/N100A, H78A/N100D and H78A/N100H wherein the amino acid N100 is mutated into alanine, aspartic acid and histidine respectively (example 2). The double mutant of IFNAR2 H78A/N100A (example 2) showed the highest affinity of all the generated mutants (Kd of about 30 pM and lower, see examples 5 and 6).

FIG. 4 shows that in the presence of 2.5 nM of wild type IFNAR2 EC about 20% IFNβ is bound to the soluble receptor (occluded), while in the presence of only 0.2 nM of the double mutant EC H78A/N100A 50% of IFNβ is bound and using only 0.4nM of H78A/N100A mutant EC 80% of the IFNβ is bound. The biological assay demonstrated also, that the same extent of occluded IFNβ (bound IFNβ under equilibrium conditions) and the residual antiviral activity (free IFNβ) obtainable with wild type IFNAR2 could be accomplished using about 30 fold lower concentration of the H78A/N100A IFNAR2 mutant EC. The results show also that the double modified mutants yield the best results, particularly the one in which both amino acids were mutated to alanine, H78A/N100A IFNAR2.

This result shows that the double mutated IFNAR2 occlude more effectively IFNβ and therefore administration of considerably lower amounts will be required to accomplish its carrier activity.

REFERENCES

Alam et al, Pharmaceutical Research 14:546-549 (1997).
Anfinsen, Science 181:223-230 (1973).
Ausubel et al, Current Protocols in Molecular Biology, Greene Publications and Wiley Interscience (New York, 1987-1992).
Baron et al, Antiviral Res. 24:97-110 (1994).
Baron, et al, J. Am. Med. Assoc. 266:1375-1383 (1991).
Christofinis, G. J Journal of General Virology 52:169-171 (1981).
Colamonici et al, J. Immunol. 148:2126-2132 (1992).
Colamonici et al, J. Biol. Chem. 268:10895-10899 (1993).
Curtis, B. M., Proc. Natl. Acad. Sci. 88:5809-5813 (1991).
Domanski et al, The Journal of Biological Chemistry 270:6 (1995).
Duncan et al, J. Exp. Med. 184:2043-2048 (1996).
Dron et al, "Interferon a/f3 gene structure and regulation" in Interferon: Principles and Medical Applications, Baron et al, Editors, (University of Texas Medical Branch: Galveston, Tex., 1992) pp. 33-45
Edington, S. M., "Biotech Products as Drug Leads" BioTechnology 13:649 (1995).
Fierlbeck et al, Journal of Interferon and Cytokine Research 16:777 (1996).
Grantham, Science 185:X62-X64 (1974).
Grazia Cusi, Mo, Immunotechnology 3:61-69 (1997).
Ibanez, C. F., EMBO Journal 10:2105-2110 (1991).
Jacobs L, et al. Arch Neurol June 1987; 44(6):589-95.
Keown, W. A., Methods in Enzymology 185:527-537 (1990).
Lengyl, P. Ann. Rev. Biochem. 51:251-282 (1982).
Lutfalla et al, EMBO Journal 14:5100-5108 (1995).
Novick et al, FEBS Lett. 314:445-448 (1992).
Novick et al, Cell 77:391-400 (1994).
Novick et al, J. Leuk. Bio. 57:712-718 (1995).
Piehler and Schreiber J. Mol. Biol. 1999A 289, 57-67.
Piehler and Schreiber J. Mol. Biol. 1999B 294, 223-237.
Piehler and Schreiber Analytical Biochemistry 289, 173-186.
Platanias et al, 1993 J. Immunology 150: 3382-3388.
Platanias et al, 1996 J. Biol. Chem. 271: 23630-3.
Salmon et al, 1996 Journal of Interferon and Cytokine Research 16: 759.
Sharf et al, 1995 J. Biol. Chem. 270: 13063-9.
Tan et al, 1973. J. Exp. Med. 137: 317-330.
Uze et al, 1990 Cell 60: 225-34.
Yang et al, 1996 J. Biol. Chem. 271: 8057-61.
Yan et al., 1996 Mol. Cell Bio. 16: 2074-82.

The invention claimed is:

1. An isolated fusion protein comprising (1) an IFNAR2 portion consisting of the sequence of SEQ ID NO: 2 and (2) an immunoglobulin portion consisting of an immunoglobulin or fragment thereof, wherein the affinity of said fusion protein for IFN-β is synergistically increased 25 to 100-fold compared to the affinity of wild type human IFNAR2 for IFN-β.

2. The fusion protein of claim 1, wherein the affinity to IFN-β is at least 30 pM.

3. The fusion protein of claim 1, wherein the affinity to IFN-β is at least 50-fold higher than the affinity of the wild type polypeptide.

4.

SEQUENCE LISTING

<160> NUMBER OF SEQ ID NOS: 4

<210> SEQ ID NO 1
<211> LENGTH: 215
<212> TYPE: PRT
<213> ORGANISM: Homo sapiens

<400> SEQUENCE: 1

Met Ala Ser Tyr Asp Ser Pro Asp Tyr Thr Asp Glu Ser Cys Thr Phe
1               5                   10                  15

Lys Ile Ser Leu Arg Asn Phe Arg Ser Ile Leu Ser Trp Glu Leu Lys
            20                  25                  30

Asn His Ser Ile Val Pro Thr His Tyr Thr Leu Leu Tyr Thr Ile Met
        35                  40                  45

Ser Lys Pro Glu Asp Leu Lys Val Val Lys Asn Cys Ala Asn Thr Thr
    50                  55                  60

Arg Ser Phe Cys Asp Leu Thr Asp Glu Trp Arg Ser Thr His Glu Ala
65                  70                  75                  80

Tyr Val Thr Val Leu Glu Gly Phe Ser Gly Asn Thr Thr Leu Phe Ser
                85                  90                  95

Cys Ser His Asn Phe Trp Leu Ala Ile Asp Met Ser Phe Glu Pro Pro
            100                 105                 110

Glu Phe Glu Ile Val Gly Phe Thr Asn His Ile Asn Val Met Val Lys
        115                 120                 125

Phe Pro Ser Ile Val Glu Glu Glu Leu Gln Phe Asp Leu Ser Leu Val
    130                 135                 140

Ile Glu Glu Gln Ser Glu Gly Ile Val Lys Lys His Lys Pro Glu Ile
145                 150                 155                 160

Lys Gly Asn Met Ser Gly Asn Phe Thr Tyr Ile Ile Asp Lys Leu Ile
                165                 170                 175

Pro Asn Thr Asn Tyr Cys Val Ser Val Tyr Leu Glu His Ser Asp Glu
            180                 185                 190

Gln Ala Val Ile Lys Ser Pro Leu Lys Cys Thr Leu Leu Pro Pro Gly
        195                 200                 205

Gln Glu Ser Glu Phe Ser Glx
        210                 215

<210> SEQ ID NO 2
<211> LENGTH: 215
<212> TYPE: PRT
<213> ORGANISM: Homo sapiens

<400> SEQUENCE: 2

Met Ala Ser Tyr Asp Ser Pro Asp Tyr Thr Asp Glu Ser Cys Thr Phe
1               5                   10                  15

Lys Ile Ser Leu Arg Asn Phe Arg Ser Ile Leu Ser Trp Glu Leu Lys
            20                  25                  30

Asn His Ser Ile Val Pro Thr His Tyr Thr Leu Leu Tyr Thr Ile Met
        35                  40                  45

Ser Lys Pro Glu Asp Leu Lys Val Val Lys Asn Cys Ala Asn Thr Thr
    50                  55                  60

Arg Ser Phe Cys Asp Leu Thr Asp Glu Trp Arg Ser Thr Ala Glu Ala
65                  70                  75                  80

Tyr Val Thr Val Leu Glu Gly Phe Ser Gly Asn Thr Thr Leu Phe Ser
                85                  90                  95

```
Cys Ser His Ala Phe Trp Leu Ala Ile Asp Met Ser Phe Glu Pro Pro
            100                 105                 110

Glu Phe Glu Ile Val Gly Phe Thr Asn His Ile Asn Val Met Val Lys
            115                 120                 125

Phe Pro Ser Ile Val Glu Glu Leu Gln Phe Asp Leu Ser Leu Val
130             135                 140

Ile Glu Glu Gln Ser Glu Gly Ile Val Lys Lys His Lys Pro Glu Ile
145                 150                 155                 160

Lys Gly Asn Met Ser Gly Asn Phe Thr Tyr Ile Ile Asp Lys Leu Ile
                165                 170                 175

Pro Asn Thr Asn Tyr Cys Val Ser Val Tyr Leu Glu His Ser Asp Glu
                180                 185                 190

Gln Ala Val Ile Lys Ser Pro Leu Lys Cys Thr Leu Leu Pro Pro Gly
                195                 200                 205

Gln Glu Ser Glu Phe Ser Glx
            210                 215

<210> SEQ ID NO 3
<211> LENGTH: 215
<212> TYPE: PRT
<213> ORGANISM: Homo sapiens

<400> SEQUENCE: 3

Met Ala Ser Tyr Asp Ser Pro Asp Tyr Thr Asp Glu Ser Cys Thr Phe
1               5                   10                  15

Lys Ile Ser Leu Arg Asn Phe Arg Ser Ile Leu Ser Trp Glu Leu Lys
                20                  25                  30

Asn His Ser Ile Val Pro Thr His Tyr Thr Leu Leu Tyr Thr Ile Met
            35                  40                  45

Ser Lys Pro Glu Asp Leu Lys Val Val Lys Asn Cys Ala Asn Thr Thr
50                  55                  60

Arg Ser Phe Cys Asp Leu Thr Asp Glu Trp Arg Ser Thr Ala Glu Ala
65                  70                  75                  80

Tyr Val Thr Val Leu Glu Gly Phe Ser Gly Asn Thr Thr Leu Phe Ser
                85                  90                  95

Cys Ser His Asp Phe Trp Leu Ala Ile Asp Met Ser Phe Glu Pro Pro
            100                 105                 110

Glu Phe Glu Ile Val Gly Phe Thr Asn His Ile Asn Val Met Val Lys
            115                 120                 125

Phe Pro Ser Ile Val Glu Glu Leu Gln Phe Asp Leu Ser Leu Val
130             135                 140

Ile Glu Glu Gln Ser Glu Gly Ile Val Lys Lys His Lys Pro Glu Ile
145                 150                 155                 160

Lys Gly Asn Met Ser Gly Asn Phe Thr Tyr Ile Ile Asp Lys Leu Ile
                165                 170                 175

Pro Asn Thr Asn Tyr Cys Val Ser Val Tyr Leu Glu His Ser Asp Glu
                180                 185                 190

Gln Ala Val Ile Lys Ser Pro Leu Lys Cys Thr Leu Leu Pro Pro Gly
                195                 200                 205

Gln Glu Ser Glu Phe Ser Glx
            210                 215

<210> SEQ ID NO 4
<211> LENGTH: 215
<212> TYPE: PRT
```

-continued

```
<213> ORGANISM: Homo sapiens

<400> SEQUENCE: 4

Met Ala Ser Tyr Asp Ser Pro Asp Tyr Thr Asp Glu Ser Cys Thr Phe
1               5                   10                  15

Lys Ile Ser Leu Arg Asn Phe Arg Ser Ile Leu Ser Trp Glu Leu Lys
                20                  25                  30

Asn His Ser Ile Val Pro Thr His Tyr Thr Leu Leu Tyr Thr Ile Met
            35                  40                  45

Ser Lys Pro Glu Asp Leu Lys Val Val Lys Asn Cys Ala Asn Thr Thr
        50                  55                  60

Arg Ser Phe Cys Asp Leu Thr Asp Glu Trp Arg Ser Thr Ala Glu Ala
65                  70                  75                  80

Tyr Val Thr Val Leu Glu Gly Phe Ser Gly Asn Thr Thr Leu Phe Ser
                85                  90                  95

Cys Ser His His Phe Trp Leu Ala Ile Asp Met Ser Phe Glu Pro Pro
                100                 105                 110

Glu Phe Glu Ile Val Gly Phe Thr Asn His Ile Asn Val Met Val Lys
            115                 120                 125

Phe Pro Ser Ile Val Glu Glu Glu Leu Gln Phe Asp Leu Ser Leu Val
        130                 135                 140

Ile Glu Glu Gln Ser Glu Gly Ile Val Lys Lys His Lys Pro Glu Ile
145                 150                 155                 160

Lys Gly Asn Met Ser Gly Asn Phe Thr Tyr Ile Ile Asp Lys Leu Ile
                165                 170                 175

Pro Asn Thr Asn Tyr Cys Val Ser Val Tyr Leu Glu His Ser Asp Glu
                180                 185                 190

Gln Ala Val Ile Lys Ser Pro Leu Lys Cys Thr Leu Leu Pro Pro Gly
            195                 200                 205

Gln Glu Ser Glu Phe Ser Glx
        210                 215
```